United States Patent [19]

Sennett et al.

[11] Patent Number: 5,417,690
[45] Date of Patent: May 23, 1995

[54] SURGICAL CABLE

[75] Inventors: Andrew R. Sennett, Hanover; Brenda I. Lugo, Quincy, both of Mass.; Ronald A. Yapp, Phoenix, Ariz.

[73] Assignee: Codman & Shurtleff, Inc., Randolph, Mass.

[21] Appl. No.: 123,953

[22] Filed: Sep. 20, 1993

[51] Int. Cl.⁶ ............................................. A61F 5/04
[52] U.S. Cl. ....................................... 606/61; 606/74
[58] Field of Search ............. 606/60, 74, 103, 224–228; 128/772; 57/22, 202; 24/129 C, 129 W, 122.6

[56] References Cited

U.S. PATENT DOCUMENTS

| | | | |
|---|---|---|---|
| 1,310,232 | 7/1919 | Albaum . | |
| 2,109,517 | 3/1938 | Xenis | 24/129 W |
| 2,291,413 | 12/1942 | Siebrandt . | |
| 2,802,467 | 8/1957 | McNally . | |
| 2,959,436 | 11/1960 | Duda | 24/122.6 |
| 3,125,095 | 3/1964 | Kaufman et al. | 606/224 |
| 3,311,110 | 3/1967 | Singerman et al. | 606/226 |
| 3,527,487 | 9/1970 | Payne | 24/122.6 |
| 4,133,339 | 1/1979 | Naslund | 132/89 |
| 4,364,380 | 12/1982 | Lewis | 433/2 |
| 4,441,497 | 4/1984 | Paudler . | |
| 4,604,995 | 8/1986 | Stephens et al. . | |
| 4,625,717 | 12/1986 | Covitz . | |
| 4,643,178 | 2/1987 | Nastari et al. | 606/103 |
| 4,682,607 | 7/1987 | Vaillancourt et al. | 128/772 |
| 4,686,970 | 8/1987 | Dove et al. . | |
| 4,773,417 | 9/1988 | Moore et al. | 606/80 |
| 4,790,303 | 12/1988 | Steffee . | |
| 5,089,012 | 2/1992 | Prou | 606/225 |
| 5,092,868 | 3/1992 | Mehdian | 606/74 |
| 5,318,566 | 6/1994 | Miller | 606/60 |

FOREIGN PATENT DOCUMENTS

| | | | |
|---|---|---|---|
| 2432861 | 3/1980 | France | 606/228 |
| 1088711 | 4/1984 | U.S.S.R. | 606/225 |

OTHER PUBLICATIONS

Bekraert, *Steel Cord Catalogue*, 1982.

*Primary Examiner*—Stephen C. Pellegrino
*Assistant Examiner*—Nancy Mulcare
*Attorney, Agent, or Firm*—Michael Q. Tatlow

[57] ABSTRACT

A multistrand surgical cerclage cable having a multistrand leader is disclosed. The cable is very flexible and the leader is more malleable and stiffer than the cable allowing the leader to be shaped to be fed or directed around and between tissue in the patients body.

8 Claims, 4 Drawing Sheets

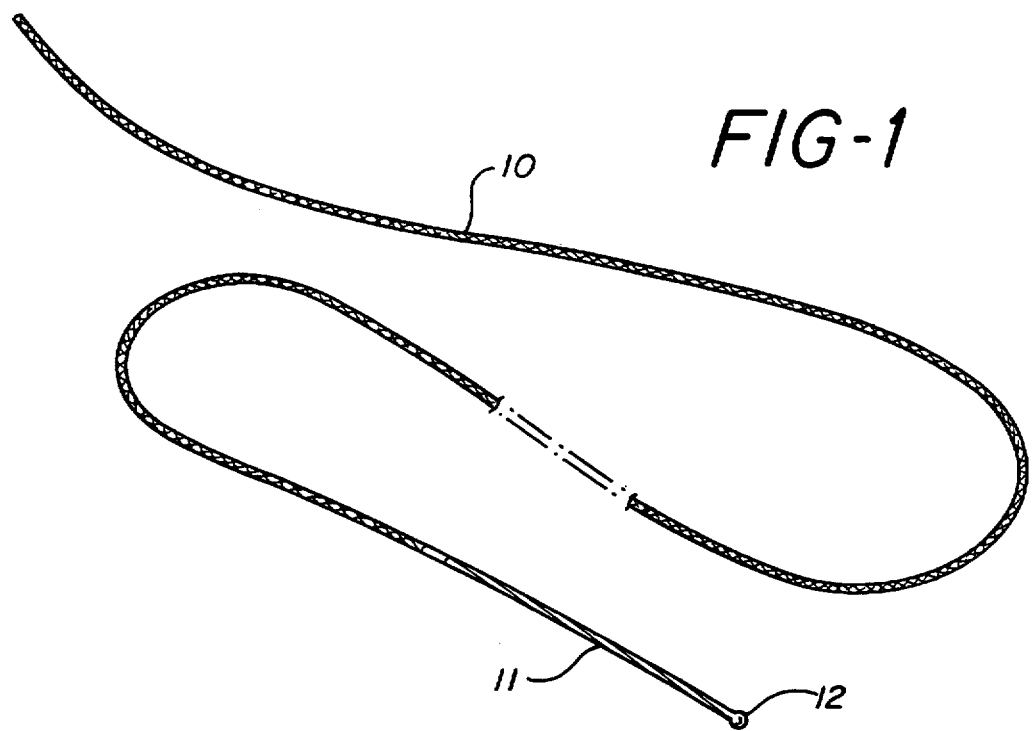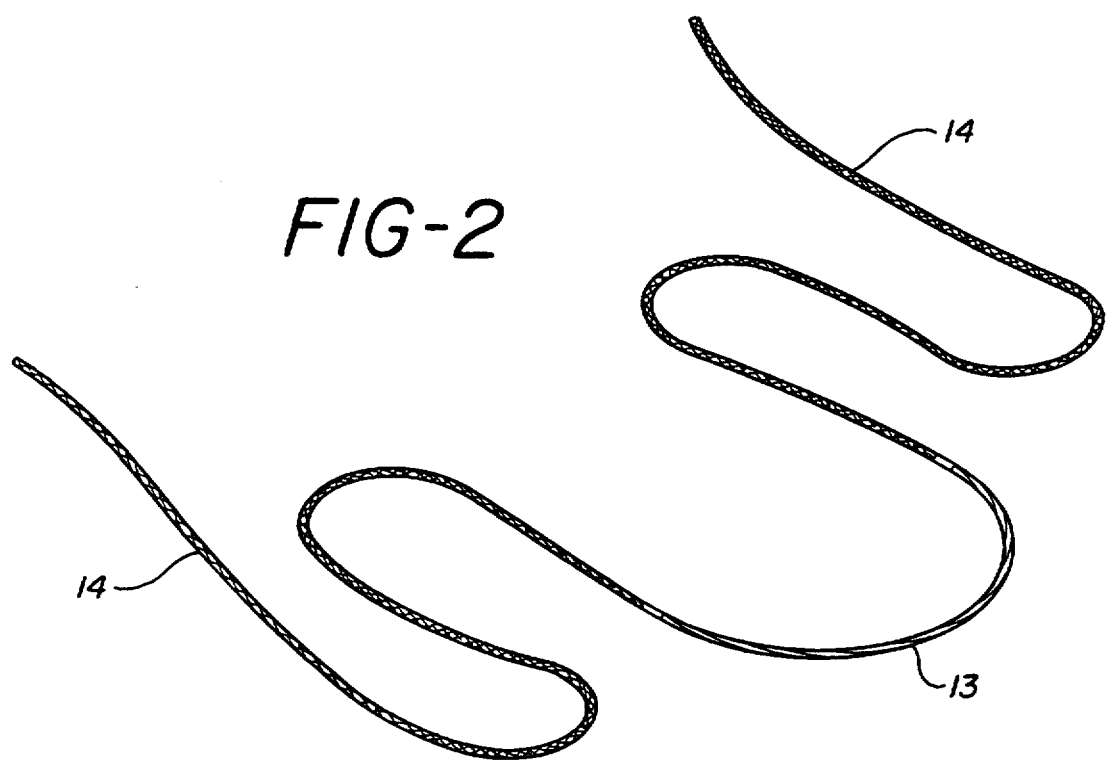

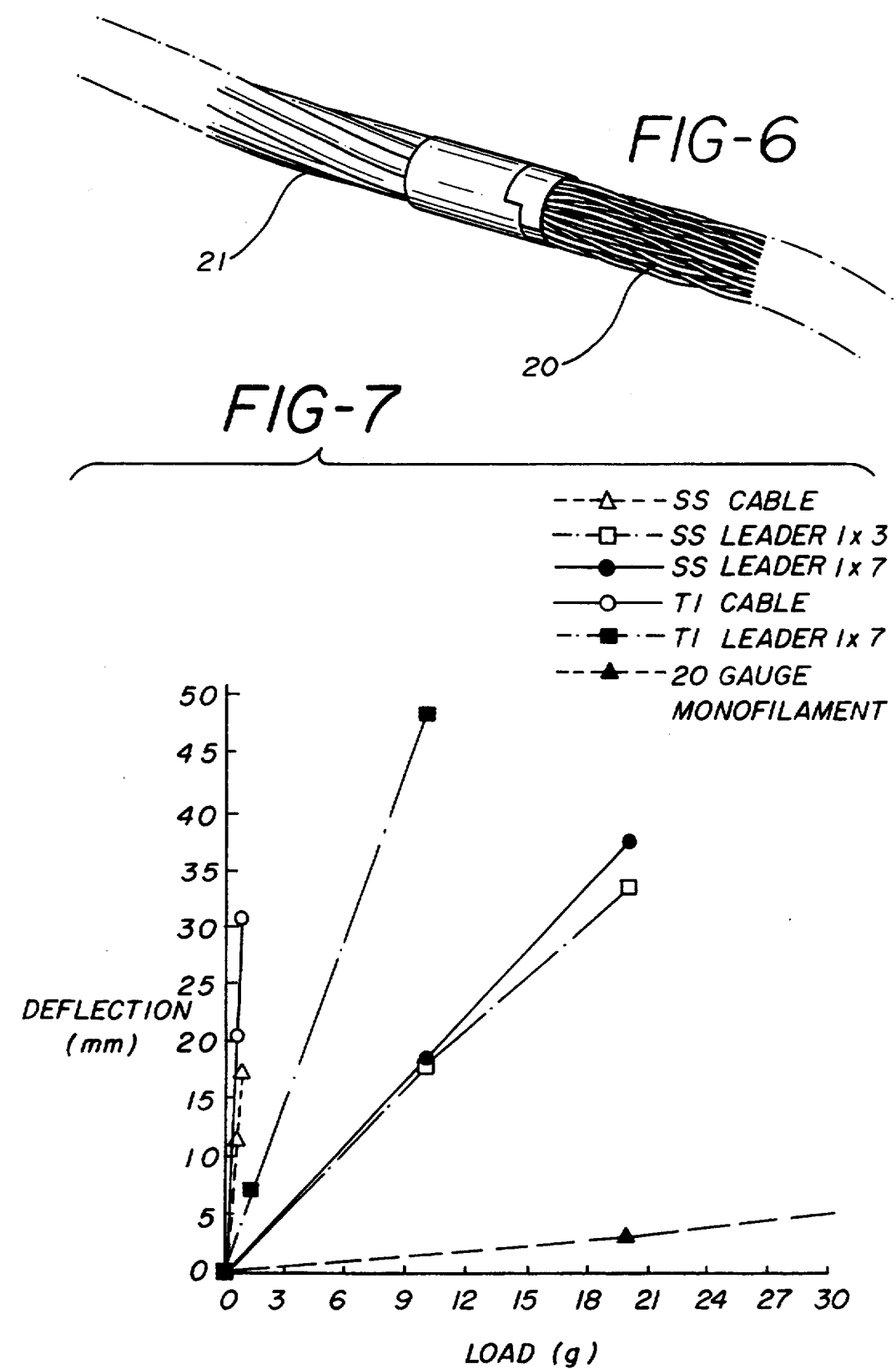

SURGICAL CABLE

BACKGROUND OF THE INVENTION

The present invention relates to surgical cables, particularly cerclage cables that are used in surgical procedures to stabilize fractures and to secure various types of prosthesis to bones.

Cerclage fixation by wires, sutures and cables has been used for some time to repair fractured bones and to secure prosthetic devices to bones, particularly in the spine. Originally, surgical fixation was achieved by stiff stainless steel wires which could be molded into shape and passed around or between various bones and then twisted together to tighten the wire around the bone or around the prosthesis. The use of surgical cable or wire devices of this type for this purpose is disclosed in the following Stephens, et.al. U.S. Pat. No. 4,604,995; Dove, et.al. U.S. Pat. No. 4,686,970 Steffee, U.S. Pat. No. 4,790,303 and Mehdian U.S. Pat. No. 5,092,868.

The wire used to repair fractured bones or to secure the prosthesis to bone have generally been monofilament stainless steel or titanium. These materials had sufficient malleability to enable the physician or operating room personnel to shape the wire into the desired configuration to pass the wire between or around bones. An example of this technique is shown in the above mentioned U.S. Pat. No. 5,092,868.

The problem with wires of this type is that they were extremely hard and stiff, and for that reason great care had to be exercised in the operating room in moving the wire around bones since it could cause serious or irreparable damage to the underlying soft tissue if the tissue was inadvertently contacted with excessive force. This is particularly true in the spinal column in procedures in which a prosthesis or a bone graft is affixed to the vertebrae to stabilize the vertebrae.

More recently, there has become available a relatively soft and flexible cable which avoids the problem of the stiff wires previously used. These new soft flexible cables have comparable strength to the stiff cables previously used. They are made with multiple wire filaments fully work hardened and twisted together to form a strand and then a plurality of these strands are twisted together around a core strand to make a strong flexible cable. These cables are a marked improvement over the wire which have previously been used. However, because of the flexibility and relatively little ductility they are difficult to form and pass around bone segments in the vertebrae or around bones that are not readily accessible.

SUMMARY OF THE INVENTION

The present invention provides a highly flexible cable with a leader which is significantly more malleable then the cable to enable operating room personnel to shape the leader to the desired shape to pass the leader into the proper position between or around bones. The leader is removed from the cable after the cable is secured in its desired position. The difference between the fixation portion of the cable which is used to secure the bone or prosthesis to bones and the leader is based on a difference in material condition. The malleable leader portion of the cable is significantly more ductile then the fixation portion of the cable. The stiffness of the multistrand leader should be greater than the stiffness of the cable, and also be significantly less than stiffness of a 20 gauge (0.032 in) monofilament wire that has been previously employed as a leader for a cerclage cable. This allows the leader portion of the cable to be formed by hand into in the desired shape, passed into the proper position, and the fixation portion can then be pulled to fully expose and place the fixation portion in the desired position, and the leader can then be removed from the fixation portion of the cable and discarded. The fixation portion of the cable is then cinched or crimped or otherwise secured in the proper position after the correct amount of force has been applied to the cable.

BRIEF DESCRIPTION OF THE DRAWINGS

FIG. 1 illustrates a cable of the present invention with a leader at one end.

FIG. 2 illustrates a cable of the present invention with a leader in the center of the cable.

FIG. 6 is an exploded view showing a weld attachment of a leader to a cable.

FIG. 7 is a graph showing the difference in stiffness in various cables and leaders.

DETAIL DESCRIPTION OF THE INVENTION

Figure 3:
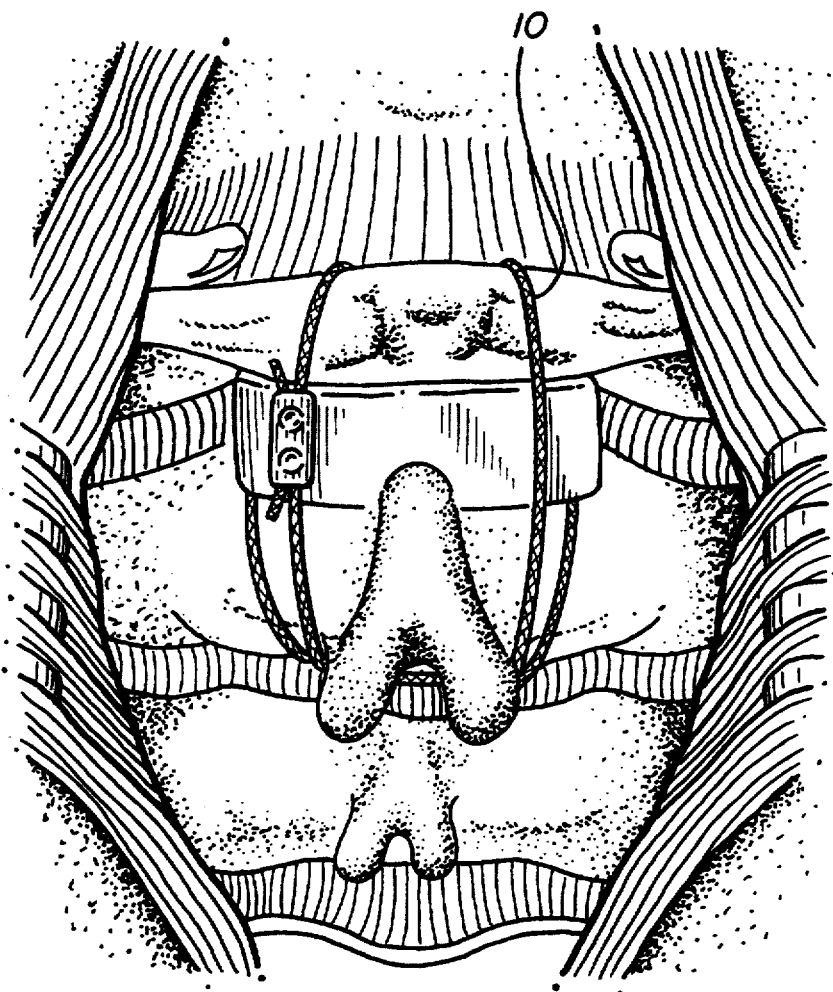
FIG. 3 illustrates the use of the cable in securing a prosthesis to the spine.

The surgical cable of the present invention is generally referred to as cerclage cable. As previously indicated, such cables are used to secure fractured bones together and are also used to secure various prosthesis or grafts to bones. One of the major uses of cerclage cables of this type is for spinal fixation. In such use, various prosthesis, or bone is secured to the vertebra to fuse vertebrae or to stabilize the vertebrae. Examples of these procedures are disclosed in the above mentioned U.S. Pat. Nos. 4,686,970; 5,092,868 and 4,790,303 and 4,604,995. In a fixation or stabilization procedure, the prosthetic device is placed in proximity to the vertebrae and usually overlies multiple vertebrae. A fixation wire or cerclage cable is passed around the vertebrae and the two ends of the wire are then twisted to secure the device to the vertebrae. In some instances, the ends of the wire or cable are passed through the cinch, pressure is applied to the cinch to crimp the cinch against the wire or cable, thereby holding the wire or cable in position.

The flexible cable used in the present invention is made by forming individual strands by twisting together multiple individual wire filaments. Usually, the filaments are in a fully work hardened condition. The wire filaments are in a configuration with a core filament and additional filaments twisted around the core filament in a first helical direction. A number of these strands are then arranged in a substantially symmetrical pattern about a central core strand in concentric rings and then twisted together in a second helical direction which is opposed to the helical direction of the individual strands. If this technique is used, any filament failure is more likely to occur in the outer surface of the cable where it can be more easily detected.

In a preferred titanium cable configuration, each strand is made up of seven filaments and the cable, six filaments twisted around a central core filament. The filaments are 0.0025 inch in diameter. The cable has 18 strands arranged in two concentric rings which are twisted together around a core strand to form the cable. After the strands are twisted into the cable, the cable may be swaged to flatten the circumference and increase the contact or wearing surface of the cable. A preferred titanium cable has a core strand made with seven filaments (1×7) left hand lay with 10 to 12 turns per inch. Six additional strands of the same construction are twisted around the core strand, right hand lay, 5.5 to 6.5 turns per inch to form a 7×7 core. The finished cable has one 7×7 core with twelve 1×7 outer strands, each outer strand having right hand lay, 10 to 12 turns per inch, and arranged around the core with a left hand lay 2.8 to 3.4 turns per inch. The leader is a 1×7 right hand lay, 2.5 to 4.75 turns per inch, made from filaments with a diameter of 001 to 0.0113 inches.

The diameter of the individual filaments in the strands range in size of approximately 0.0005 inches to 0.005 inches (approximately 0.013 mm to 0.127 mm). The individual filaments are made of metal, preferably stainless steel or titanium alloy commonly referred to as Ti—6Al—4V. Pure titanium and other biocompatible alloys of titanium or other metals may also be employed. The advantage of titanium over the stainless steel is that the titanium wires are compatible with magnetic residence imaging (MRI) techniques. Other biocompatible high strength metals, such as chrome-cobalt alloys may also be used.

Generally, the diameter of titanium filaments range in size from 0.0015 inches to 0.005 inches (approximately 0.38 mm to 0.127 mm) whereas the diameter of the stainless steel filaments generally range in size from 0.0005 inches to 0.005 inches (approximately 0.13 mm to 0.127 mm).

The preferred size for the titanium and the stainless steel cable is a diameter of approximately 0.0025 inches or 0.65 mm.

As previously indicated, the fixation cable is extremely flexible. This flexibility offers certain advantages in use but creates difficulty in placing the cable in the desired position during the particular surgical procedure. This difficulty can be overcome by using a leader attached to the cable. The leader is somewhat stiffer than the cable and can be shaped and will hold its shape so that it may be passed around bone.

The leader portion of the cable, generally is not as complicated a construction as the fixation portion of the cable as it will not need the same degree of flexibility as the fixation portion of the cable. Generally, the typical leader portion of the cable would have, seven ends, six filaments twisted around a central filament, and each of the filaments having a diameter of approximately 0.010 inches. The leader portion could have more filaments, e.g. 21, both the simplest construction is often most economical.

The fixation portion of the cable, that is that portion of the cable that is actually used for fixation, can be attached to the leader portion of the cable by a variety of different techniques. The leader can be welded or adhesively secured to the fixation portion of the cable. It is also possible to use shrink tubing to secure the leader to the cable. The tubing is positioned over the leader and fixation portion of the cable, which are in end to end contact, and the tubing is heated to shrink the tubing and secure the leader to the cable. It is also possible to make a single cable and then by heat treatment or annealing the fixation portion of the cable in a different manner then the leader portion of the cable, the desired malleability or stiffness can be obtained for the leader portion of the cable. This is particularly useful in a cable which has a leader at one end.

The cerclage cable of the present invention shown in FIG. 1 has a fixation portion 10 attached to a leader portion 11. There can be an bead 12 on the end of the leader portion to ensure that there are not sharp points on the end of the leader that could accidently damage soft tissue when the leader is being positioned around a bone or vertebrae.

In the embodiment shown in FIG. 2, the leader portion 13 is positioned between two fixation portions 14 of the cable. A cable of this type finds particular usefulness in securing prosthesis or bone grafts to vertebrae. The central leader can be shaped into a loop, passed under a vertebrae, and the loop can then be grasped with the appropriate instrument, the fixation portion of the cable pulled into the desired position and the leader can be removed from the fixation portion of the cable and both fixation cables crimped or cinched together to secure the prosthesis or bone graft to the vertebrae.

The use of cables to secure a prosthesis to the spine is illustrated in FIG. 3. The cable can be secured with cinches as shown in FIG. 3.

Figure 4:
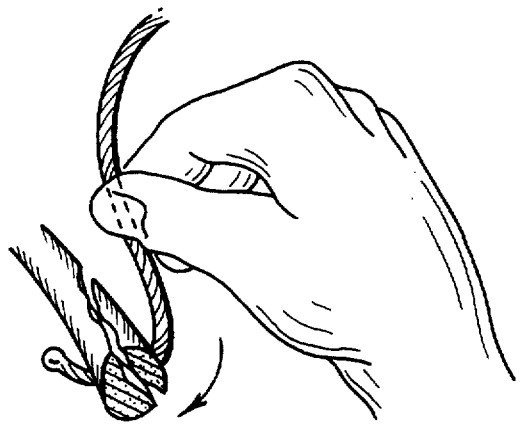
FIG. 4 and FIG. 5 illustrate the use of the leader to pass a cable around bones.
Figure 5:
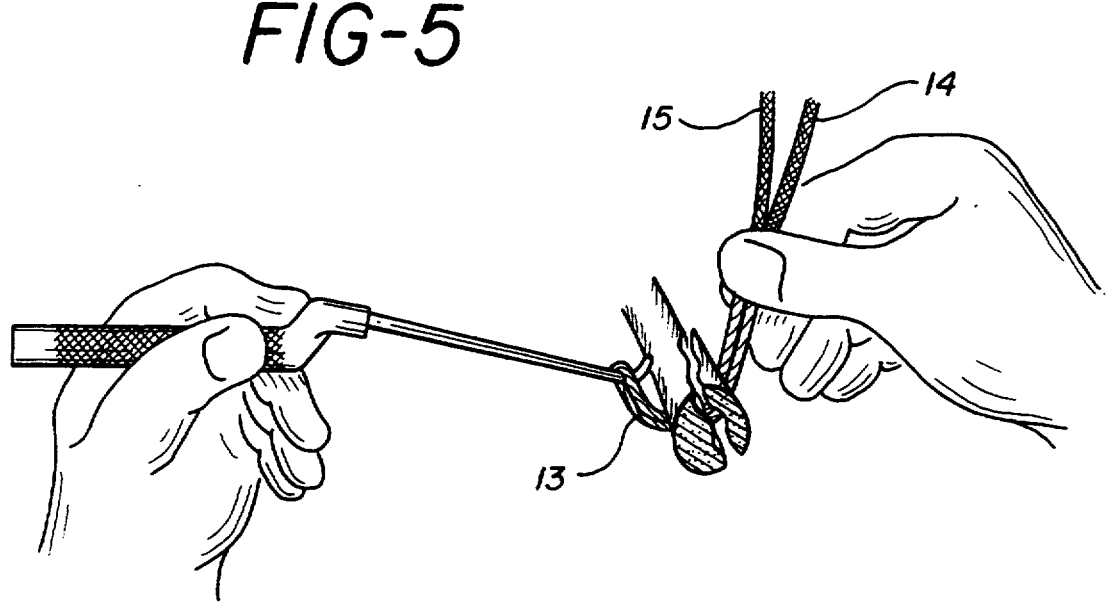

The technique of passing the cable around bones is shown in FIG. 4 and in FIG. 5. In FIG. 4 a cable with a leader 11 and beaded end 12 is first shaped into a desired configuration to readily passed around the bone. The cable is then passed around the bone and the leader will subsequently be removed and the fixation portion of the cable will be joined with a cinch mechanism.

FIG. 5 shows the use of a central leader passing a fixation wire around a bone. A loop can be formed in the central leader which is also shaped and a curved configuration to be passed around the bone and then secured with an instrument and then the fixation portions of the cable 14 and 15 are pulled around the bone and secured.

The preferred method of attaching the leader to the fixation cable is illustrated in an exploded view in FIG. 6. FIG. 6 shows a multi-strand fixation cable 20 which has approximately 133 individual filaments secured to a leader 21 which has approximately 7 filaments. Each one of leader filaments is considerably larger then the individual filaments of the fixation portion of the cable. It should be noted that it is preferred to have the leader portion of the cable have the same diameter of the fixation portion of the cable. This prevents the possibility of the fixation portion of the cable from being caught on a bone or other tissue because of the difference in the diameter of the cable if the leader portion was smaller in diameter than the fixation portion of the cable. If the fixation portion of the cable is the same diameter as the leader portion, there is little possibility that the fixation cable will be caught on a bone or other tissue as it is being passed through tissue.

There is a difference in both the stiffness between the fixation portion of the cable and the leader portion of the cable, and the malleability of the fixation portion of the cable and the leader portion of the cable. The greater malleability of the leader portion enables the leader portion of the cable to be shaped into a desired configuration to pass around bones and between the vertebrae. Malleability is not a desired characteristic of the fixation portion of the cable of the present invention. The fixation portion of the cable is more flexible, and not as malleable as the leader and would not hold its shape. The leader should not be so stiff that it would be spring like. A stiff spring like leader can cause injury if it snaps or flexes against soft tissue.

The stiffness of the cable and the leader can be demonstrated by a simplified elastic beam model. The stiffness, K, of the cable and the leader can be expressed as the deflection of the sample per unit of force within the elastic limit applied to a free end of length of the sample when the other end of the sample is held in a fixed position. The amount of force necessary per unit of deflection increases with increasing stiffness and the amount of movement of the sample per unit of force increases with decreasing stiffness.

The K values of the leader of the present invention should be at least 0.15 mm and deflection per gram of force of a 25.4 mm lengths of leader. Generally, the K values are between 0.15 mm/gm and 0.75 mm/gm. The stiffness, K, of the cable is between about 2 mm/gm and 6 mm/gm.

The preferred method of attaching the leader portion of the cable to the fixation portion of the cable is with a butt welding technique. In this process the first step is formed by welding a bead at the end of each of the fixation portion of the cable and the leader portion of the cable. Each beaded end is then swaged into a generally circular configuration. The two ends are then brought into contact with each other and butt welded to form a weld which is sufficiently strong to enable the leader to be passed in the desired position and the leader to be pulled to bring the fixation portion of the cable into the desired position.

We claim:

1. A surgical cerclage cable comprising a multistrand fixation portion and a longitudinally attached multistrand leader portion, said fixation portion having a stiffness of from 2 to 6 millimeters of deflection per gram of force applied to a free end of a 25.4 millimeter length of the cable while the opposite end of said length is held in a fixed position, said leader portion having a stiffness of from 0.15 to 0.75 millimeters of deflection per gram of force applied to a free end of a 25.4 millimeter length of the cable while the opposite end of said length is held in a fixed position, said leader portion and said fixation portion having substantially the same diameter.

2. The surgical cerclage cable of claim 1 in which the fixation portion of the leader portion are made of the same metal.

3. The surgical cerclage of claim 1 in which the fixation portion of the cable is made of 18 strands arranged in two concentric rings around a central core strand and the leader portion of the cable is made of six strands arranged around a central core strand, and each strand in the fixation portion and the leader portion having seven filaments.

4. The surgical cerclage cable of claim 3 in which the filaments in the leader portion and the fixation portion are stainless steel.

5. The surgical cerclage cable of claim 4 in which the filaments have a diameter of between 0.0005 inches and 0.005 inches.

6. The surgical cerclage cable of claim 3 in which the filaments in the leader portion and the fixation portion are made from the titanium alloy Ti—6Al—4V.

7. The surgical cerclage cable of claim 6 in which the filaments have a diameter of from 0.0015 inches to 0.005 inches.

8. A surgical cerclage cable comprising a multistrand fixation portion and longitudinally attached multistrand leader portion, said fixation portion comprising nineteen strands twisted together in a first helical direction, each of said strands comprising seven individual filaments twisted together in a second helical direction opposed to said first helical direction, said individual filaments in said fixation portion having a diameter in the range of from 0.0005 to 0.005 inches, said leader portion comprising 3 to 7 filaments twisted together, said individual filaments in said leader portion having a diameter of from 0.005 to 0.015 inches, said fixation portion having a stiffness of from 2 to 6 millimeters of deflection per gram of force applied to a free end of a one inch (25.4 millimeters) length of said fixation portion while the opposite end of said length is held in a fixed position, said leader portion having a stiffness from 0.15 to 0.75 millimeters of deflection per gram of force applied to a free end of a one inch (25.4 millimeter) length of said leader portion while the opposite end of said length is held in a fixed position.

* * * * *

UNITED STATES PATENT AND TRADEMARK OFFICE
CERTIFICATE OF CORRECTION

PATENT NO. : 5,417,690

DATED : May 23, 1995

INVENTOR(S) : Sennett et al.

It is certified that error appears in the above-identified patent and that said Letters Patent is hereby corrected as shown below:

Column 6, claim 8, line 24
add "a" between "and" and "longitudinally"

Signed and Sealed this

Fifteenth Day of August, 1995

Attest:

BRUCE LEHMAN

Attesting Officer        Commissioner of Patents and Trademarks